United States Patent [19]

Gueret

[11] Patent Number: 4,758,217
[45] Date of Patent: Jul. 19, 1988

[54] METHOD FOR OBTAINING A CRYOGENIC TREATMENT EFFECT FOR THE CUTANEOUS COVERING AND A UNIT FOR THE IMPLEMENTATION OF THIS METHOD

[75] Inventor: Jean-Louis H. Gueret, Paris, France

[73] Assignee: L'Oreal, Paris, France

[21] Appl. No.: 46,197

[22] Filed: May 5, 1987

[30] Foreign Application Priority Data

May 5, 1986 [FR] France .................. 86 06453
Apr. 17, 1987 [FR] France .................. 87 05532

[51] Int. Cl.$^4$ ............................. A61F 7/00
[52] U.S. Cl. ........................ 604/49; 604/291; 128/399
[58] Field of Search ............... 604/291, 290, 49; 128/402, 82.1, 399

[56] References Cited

U.S. PATENT DOCUMENTS 3,752,155  8/1973  Blinoff, Jr. et al. .
3,929,131  12/1975  Hardwick ............... 604/291
4,381,025  4/1983  Schooley .

FOREIGN PATENT DOCUMENTS 2360031  2/1978  France .
2563728  11/1985  France .

Primary Examiner—Stephen C. Pellegrino
Attorney, Agent, or Firm—Cushman, Darby & Cushman

[57] ABSTRACT

A method of and apparatus for applying at least one active substance to the skin simultaneously with the production of a cryogenic treatment effect. A liquefied refrigerant gas is released from a pressurized aerosol-type container simultaneously with or in sequence with the application of an active substance. The impregnated absorbent pad is then applied to the skin with the refrigerant gas evaporating slowly to produce the desired cryogenic effect while leaving a film of the active substance on the skin.

The absorbent element may be provided on an applicator which itself may be mountable to the pressurized container to act as a control for the container and also to permit the directing of the stream of liquefied gas from a valve at the container outlet to either the active or to the reverse surface of the absorbent pad. The container may be carried by a base which also comprises a reserve of absorbent pads. The applicator can hold the absorbent pad in a required configuration such as a domed configuration.

11 Claims, 4 Drawing Sheets

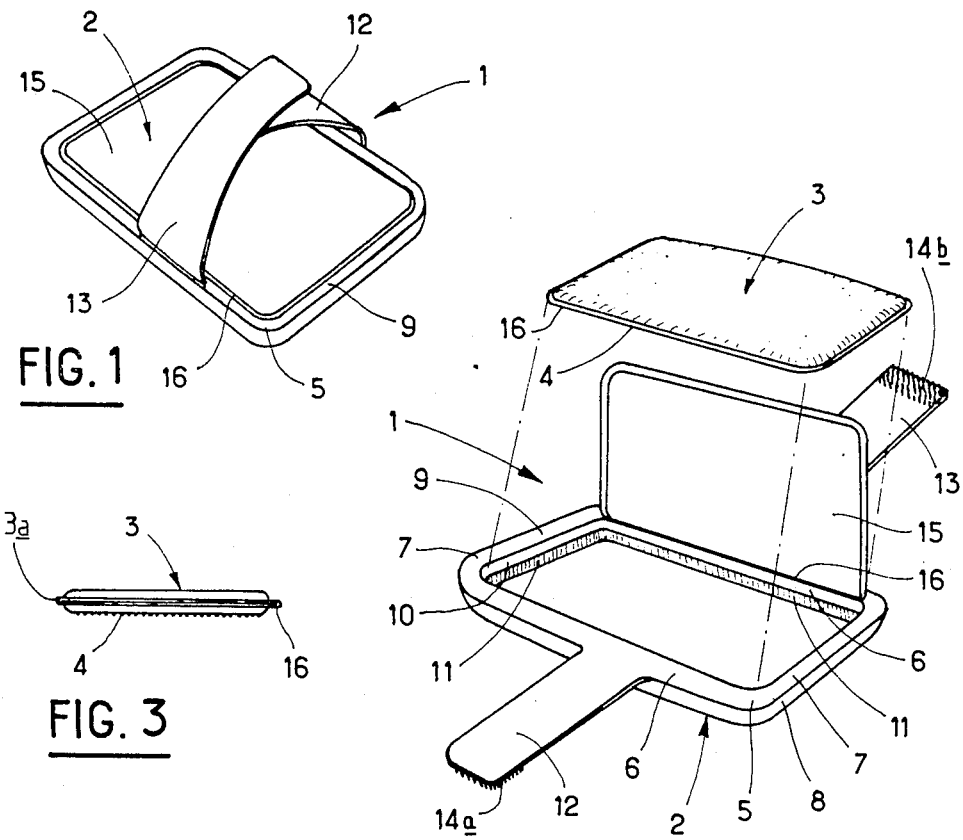

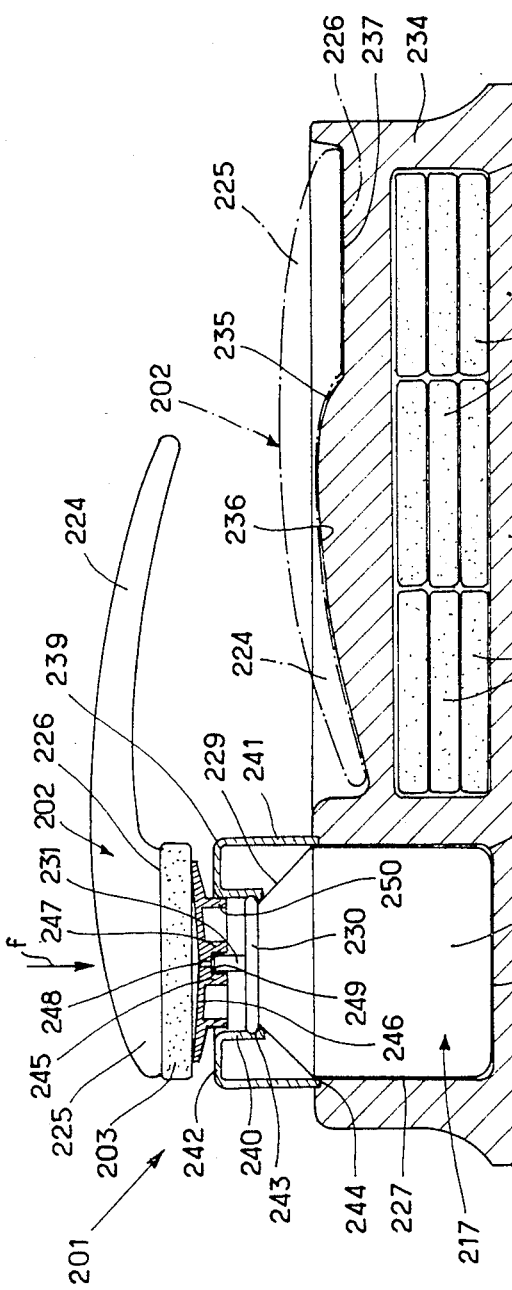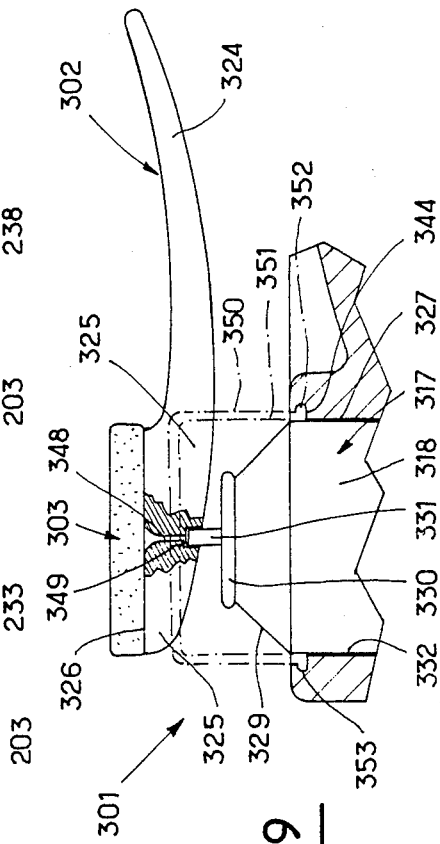

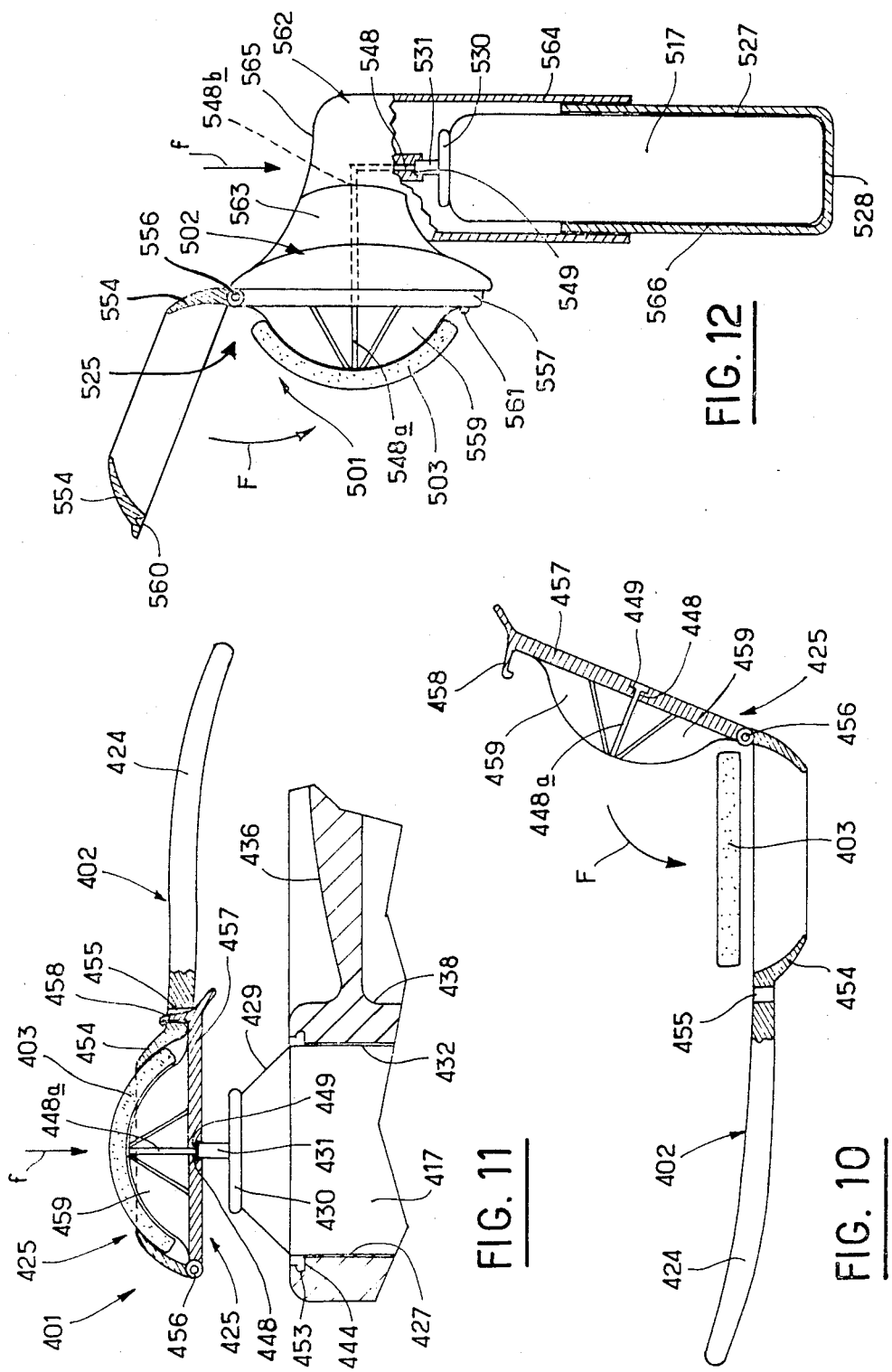

METHOD FOR OBTAINING A CRYOGENIC TREATMENT EFFECT FOR THE CUTANEOUS COVERING AND A UNIT FOR THE IMPLEMENTATION OF THIS METHOD

The present invention relates to a unit for applying at least one active substance on the cutaneous covering by means of a cryogenic fluid so as to profit simultaneously from the well known effect of cold on the skin, in particular for stimulating it: the present invention also relates to a unit for the implementation of this method.

Various applicator types are known which are used in cosmetology and, in general, for all skin treatments requiring a cryotherapeutic effect. One uses in particular, applicators constituted by a bag containing chilled substances or cryogenic mixtures.

From the French Pat. No. 2 563 728, an applicator is also known with a cryotherapeutic effect allowing the skin to be massaged by a vaso-constricting effect followed by vaso-dilatation; this applicator is constituted by a spherical container, provided with a half-flat allowing easy application to the skin. This container contains a refrigerating mixture which is maintained at a low temperature and it is obturated by a flexible nipple provided, at its end, with a metallic cap facilitating pointwise application on the skin.

Such cold massaging applicators do not make it possible to cause the penetration into the skin of active substances of the type of hydrating, regenerating or similar substances. In point of fact, at the time of application, one partition is always interposed between the refrigerating mixture and the skin.

To be sure, from the European Pat. No. 17 595, cosmetic products are known taking the form of frozen blocks or tablets, which can be directly applied on the skin and each allowing multiple applications, the vaso-constricting effect of the cold coming to be added to the action, properly so-called of these cosmetic substances; thus, a fast penetration of the cosmetic products into the epidermis is ensured. It will, however, be found during use that this mode of application has disadvantages: firstly, the cosmetic blocks or tablets must be preserved in a refrigerator; secondly, during application, a film is formed of the substance which has come into contact with the epidermis which very rapidly forms a liquid, which does not guarantee that the active substance has really penetrated into the epidermis.

The present invention proposes an altogether original method for stimulating the epidermis by the action of cold, whilst causing an active skin care product to penetrate into the latter. The inventor has discovered, in point of fact, that by successively or simultaneously impregnating an absorbing element by a dose of at least one active stimulating substance and by a dose of at least one liquefied refrigerant gas, delivered in its liquid state at the outlet of a pressurised container, and by applying this element having absorbed the combination of the active substance or substances-liquefied refrigerant gas (or gases) to the skin, it proved possible to obtain the desired effects. In the case of a simultaneous impregnation, provision can advantageously be made for the pressurised container containing the refrigerant gas (or gases) to contain also the active substance or substances, the latter being found in a form allowing its (or their) dispensing by means of the outlet valve of the pressurised container.

Whilst the liquid substance emerging from the pressurised container could not be directly applied to the skin on emerging from the said container because at that moment, it is at a very low temperature of the order of $-42°$ C., as a result of the expansion of the gas which would on the one hand, burn the skin and would not, on the other hand, produce a durable cold effect, it will be observed that when there is a transfer on to an absorbent element—which comprises preferably a surface rendered super-absorbent, for instance by flocking—the application on the skin becomes altogether tolerable, not producing any burning of the latter and that it remains durable because the evaporation of the liquefied gas is much slower because it is trapped in the absorbent element.

The implementation of the method therefore takes place in accordance with the following process: the liquefied gas having impregnated the absorbent element, slowly evaporates in the air and, as has been indicated, thus generates a bearable and durable cryogenic effect on the skin; the active substances then remain in place and penetrate into the skin, thus stimulated by the cryogenic effect.

The active substance dissolved in a hydro-alcoholic or aqueous medium can be solidified, frozen under the effect of cold, and is liquefied on application to the skin.

The object of the present invention is, therefore, firstly a method for applying at least one active substance on the cutaneous covering simultaneously producing a cryogenic treatment effect, characterised in that the impregnation of an absorbent element is effected on the one hand by the said active substance (or substances) and on the other hand by at least one liquefied refrigerant gas emerging in the state of a liquid jet from a pressurised container of the "aerosol can" type, wherein it (or they) was (or were) stored, and that the said absorbent element is subsequently applied on the cutaneous covering, the refrigerant gas (or gases) evaporating slowly, producing the desired cryogenic effect and by leaving a film of the said active substance (or substances) on the said cutaneous covering.

In accordance with a first mode of embodiment of the method according to the invention, one stores in the pressurised container containing the liquefied gas (or gases), the active substance (or substances) which then is (or are) in a form allowing its (or their) dispensing by the outlet valve of the said pressurised container.

In accordance with a second mode of embodiment of the method according to the invention, the active substance (or substances) and the liquefied refrigerant gas (or gases) are stored separately and they are transferred simultaneously or successively, in particular in the order indicated to the absorbent element.

In the two cases, provision can be made for storing with the liquefied refrigerant gas (or gases), at least one non-cryogenic volatile substance capable of solubilising the active substance (or substances) (or at least one cosmetically acceptable organic solvent), the said liquefied refrigerant gas (or gases) forming a long lasting phase, so that the resultant composition ejected from the pressurised container should comprise a large quantity of the gas in its liquid state, the said volatile non-cryogenic substance (or substances) evaporating when the cutaneous covering reassumes its normal temperature.

Preferably, the non-cryogenic substance (or substances) are introduced into the pressurised container at a rate of 3 to 35% by weight, in particular 10 to 30% by weight, in relation to the weight of the liquefied refrigerant gas (or gases).

The liquefied refrigerant gas (or gases) are in particular chosen from the aliphatic halogenated hydrocarbons, such, for instance, as trichlorofluoromethane, dichlorodifluoromethane, chlorodifluoromethane, chloro-1 difluoro-1,1 ethane or a mixture of these substances.

One chooses, in particular, as a volatile non-cryogenic substance, a volatile silicone such, for instance, as a cyclic polydimethylsiloxane, mentioned in the "CTFA COSMETIC INGREDIENT DICTIONARY", 3rd edition under the name of "CYCLOMETHICONE".

As the active substance, one chooses, in particular, a skin care substance taken from the group formed by the hydrating, regenerating, anti-wrinkle, anti-acne, anticellulitic, hyperaemic and firming agents.

The active substance can take the form of an aqueous or hydroalcoholic solution and the phase containing the active substance can take a frozen form at the time of use.

In accordance with a particularly worthwhile mode of embodiment of the method according to the present invention, one uses an absorbent element for the application, which is made of a plastic foam or felt type material and whose absorptive capacities have been improved by the flocking of its surface intended to receive the cryogenic treatment composition.

However, for the application, one can also use an absorbent element which is constituted by cellulose or cotton wadding.

It is also advantageous for the absorbent element to be fixed to an applicator, the said applicator being made of an insulating material and constituting, together with the absorbent element, an applicator device.

The object of the present invention is also a unit for the implementation of the method defined above, this unit being characterised in that it comprises:
  a pressurised container of the "aerosol can" type containing at least one liquefied refrigerant gas;
  at least one applicator device carrying an absorbent element intended to come into contact with the cutaneous covering, once it has been soaked by a jet of the liquid emerging from the said pressurised container and by the active substance (or substances) intended to be applied to the cutaneous covering, which is (or are) stored separately or contained in the said pressurised container then taking a form allowing it (or them) to be dispensed by means of the outlet valve of the said pressurised container.

The pressurised container can, in certain conditions of implementation of the method of the invention, contain apart from the liquefied refrigerant gas (or gases), at least one volatile non-cryogenic substance capable of solubilising the active substance (or substances) applied separately on the absorbent element, the said liquefied refrigerant gas (or gases) forming a long lasting phase.

The preferred conditions relating to the preferred ingredients, as well as, if applicable to the proportions of the constituents of the composition introduced into the pressurised container, have been indicated above.

Also as indicated above, the absorbent element can be fixed to an applicator, the applicator comprising on its opposite side to that carrying the absorbent element, the means for holding the applicator device thus formed.

Provision can in particular be made for means, as the holding means, allowing the user's hand to be kept flat on the face of the receptacle or base opposite to that of the absorbent element, these holding means being advantageously adjustable. The holding means may also consist of a handle allowing the applicator to be more easily manipulated.

In accordance with a particular mode of embodiment according to the invention, the pressurised container is provided with a dispensing valve, at the outlet whereof, there is fitted a dispensing head whose movable part receives an end fitting having a porous end face in the form of a grill or strips serving as a jet moderator to allow an easier distribution of the liquid jet emerging from the pressurised container on to the absorbent element.

Moreover, provision can advantageously be made for the applicator to constitute a means for operating the outlet valve of the pressurised container.

For this purpose, the applicator can comprise a duct capable of being made to communicate with the outlet of the valve of the pressurised container and directing the liquid jet emerging from the latter towards the absorbent element, the said duct issuing in a bore capable of receiving the said outlet valve.

In a second mode of embodiment, the duct is cut in a sole of the applicator which is intended to receive or whereon there comes to be fitted the absorbent element, this latter receiving the cryogenic treatment composition at its opposite surface to that intended to come into contact with the cutaneous covering.

The absorbent element can be detachably fixed on the applicator for instance by a velcro type system or by a self adhesive system, or the absorbent element can be placed into the applicator constituted on the one hand by a cup shaped opening without a bottom against which it bears with its edge and whence it emerges in its central portion, and on the other hand, by a top provided with fins ensuring the curving of the said absorbent element when it is fixed on the opening. Provision can be made in particular for the duct directing the liquid jet emerging from the pressurised container to be cut in the back of the sole and to be extended beyond the latter by a tube whereon there bear the shaping fins.

In accordance with another worthwhile mode of embodiment, the sole comprises a hollow element provided with an external wall zone serving as a push button and with an extension capable of coming to surmount the upper portion of the pressurised container, the push button being situated substantially above the valve stem of the pressurised container.

It may also be useful to make provision for the pressurised container to be accommodated in a base serving as a supply reserve for a plurality of absorbent elements and/or offering a hook up surface for the applicator device.

To render the object of the present invention more readily understood, there will be described below six modes of embodiment represented in the attached drawings on a purely illustrative and non-restrictive basis.

In these drawings:

FIG. 1 is a view in perspective of a first mode of embodiment of the applicator-device according to the present invention, in the ready for use position;

FIG. 2 is a view in an exploded perspective of the applicator-device of FIG. 1;

FIG. 3 is a side view of the absorbent pad of the applicator-device of FIG. 1,;

FIG. 4 shows the applicator of FIG. 1 in perspective in the position it occupies to receive the cryogenic treatment composition, the pressurised container from which the said composition is emerging, also being represented in this FIG. 4;

FIG. 8 is a view partly in elevation and partly in an axial cross section of a third mode of embodiment of the unit in accordance with the present invention, its applicator-device being represented in solid lines, in the position it occupies during the impregnation of the absorbent pad by a dose of the cryogenic treatment composition and, in dots and dashes in the rest position;

FIG. 9 is a view similar to FIG. 8 of its portion corresponding to the upper region of the pressurised container and to the applicator-device in the position for impregnating the absorbent pad, this Figure representing a fourth mode of embodiment of the unit in accordance with the present invention;

FIG. 10 is a view partly in elevation, partly in an axial cross section of an applicator-device according to a fifth mode of embodiment of the unit in accordance with the present invention, in the position it occupies to receive an absorbent pad;

FIG. 11 is a view similar to FIG. 9 showing the applicator-device of FIG. 10 in the position for impregnating its absorbent pad;

FIG. 12 is a view partly in elevation, partly in an axial cross section of a unit in accordance with a sixth mode of embodiment of the present invention.

Figure 5:
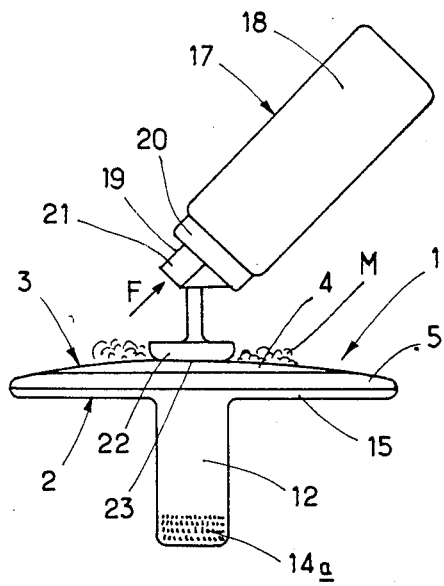
FIG. 5 shows the applicator-device and the pressurised container containing the cryogenic treatment composition in the respective positions they occupy during the impregnation of the absorbent pad by a dose of the said composition.

If reference is now made to FIGS. 1 to 5, it will be seen that 1 designates a device as a whole allowing a cryogenic fluid to be applied on the cutaneous covering which is intended to produce a "cryotherapeutic" effect during its application with a simultaneous deposit of an active hydrating substance on the said cutaneous covering.

This applicator-device 1 comprises an applicator 2 which is capable of receiving a pad 3, one side 4 of which is rendered absorbent with a view to receiving a dose of the composition. The face 4 of the pad 3 which is directed towards the outside in the fitted position of the said pad 3 in the applicator 2 therefore constitutes a sole wherewith the said applicator device 1 will be applied to the cutaneous covering for effecting its treatment by cold and the application of the hydrating agent, as a result of the massage.

The applicator 2 is made of a flexible plastic material which is also insulating, because the said applicator 2 containing the pad 3 when it has received the composition must be capable of being seized by the user's hand at its opposite side to the said pad 3 without the user feeling the effect of the cold. This material can be, inter alia, plasticized polyvinyl chloride.

The applicator 2 comprises a rectangular frame 5 with rounded corners. The cross section of each one of the sides, both longitudinal 6 and transverse 7 of the frame 5, has a substantially quadrant shaped surface so that there is constituted an external rounded side 8, a flat top 9 (the frame 5 being considered in the position it occupies in FIGS. 1 and 2 and an internal lateral side 10 perpendicular to the said top 9.

The frame 5 comprises an internal edge 11, formed all along the edge line delimited by the junction of the lateral external side 8 and the internal side 10, this edge 11 being situated in a plane parallel to the top 9.

Moreover, the latter is externally extended by two flexible tabs 12, 13 in the shape of an elongate rectangle, each connected substantially perpendicular and centrally at one of its small sides to a longitudinal side 6 of the frame 5.

The one, 12 of the flexible tabs comprises in its end region and on its opposite side to the side 9, the "hook" part 14a of an adjustable fixing system of the "velcro" type whose "velours" part 14b is carried by the end zone of the opposite tab 13 on its face situated on the side of the side 9.

The frame 5 is completed by a flap 15 of a rectangular shape, hinged to the said frame 5 along the upper internal edge line of one of its longitudinal sides 6, by a film hinge 16 obtained by moulding. The dimensions of the flap 15 are such that when the said flap 15 is in the turned down position, for instance as represented in FIG. 1, it occupies substantially all the space delimited by the internal upper edge line of the frame 5 being situated in a plane substantially identical with that of the top 9 of the said frame 5.

The pad 3 also has a rectangular shape; it is made of a plastic foam or of a felt whose face 4 has been rendered very absorbent, for instance by a flocking process. Moreover, the pad 3 is stiffened by a flat peripheral frame 3a made of a plastic material. In the case where the pad 3 is made of a plastic foam, the frame 3a can be formed by a secondary injection.

The composition which is intended to be applied to the absorbent face 4 of the pad 3 is obtained in a pressurised container 17, schematically outlined in FIG. 4, as well as in FIG. 5 wherein it is presented in its position of use.

This container comprises a body 18 having a cylindrical lateral wall, on the upper end edge whereof, there is fixed a valve carrier cup by means of crimping. In the central zone of the valve carrier cup, there is disposed a valve provided with an emergent outlet tube. The valve carrier cup, the valve and its outlet tube do not appear in the drawings: they are of an entirely conventional structure. If the outlet tube of the valve is depressed, the content of the container is exposed to the free air, which, in the case of the present invention, is projected from the latter in the form of a liquid jet, the impregnation of the pad 3 being effected with the pressurised container being up-ended, as may be seen in FIG. 5.

On the body 18, there comes to be fitted a dispensing head 19 constituted by a fixed part 20 and a movable part 21, the latter receiving an end fitting 22.

A dispensing head of this type is described in greater detail in the French Patent Application No. 85-19133; this is why the detailed description of this dispensing head will not be repeated here. It will however be indicated that the end wall 23 is constituted by a grid and that the deflector device disposed ahead of this grid which is specifically described in the above mentioned patent application, could be omitted. In the case of the present invention, the dispensing head of the type represented in the drawings has the advantage of allowing a larger surface of the pad 3 to be impregnated more rapidly.

The composition contained in the pressurised container 17 can be constituted by a 50/50 mixture of the following two refrigerant agents: trichlorofluoromethane and dichlorodifluoromethane to which there is added a volatile silicone, that is to say, the product known under the designation of "cyclomethicone" defined above in a proportion of 15% by weight in relation to the weight of the said mixture; one thus constitutes a very long lasting liquefied gas phase. An active substance with a hydrating effect is introduced into this mixture in the amount of 10% by weight in relation to the weight of the "cyclomethicone" ensuring its solubilisation.

The composition contained in the pressurised container 17 can also be constituted by a 60/40 mixture of the following two refrigerant agents: chlor-1 difluoro-1,1 ethane and chlorodifluoromethane sold by the "Dupont de Nemours" Company under the designation of "DYMEL", to which there is added an organic solvent in a proportion of 10% by weight in relation to the weight of the said mixture, capable of solubilising at least one active substance with a treatment effect.

Figure 6:
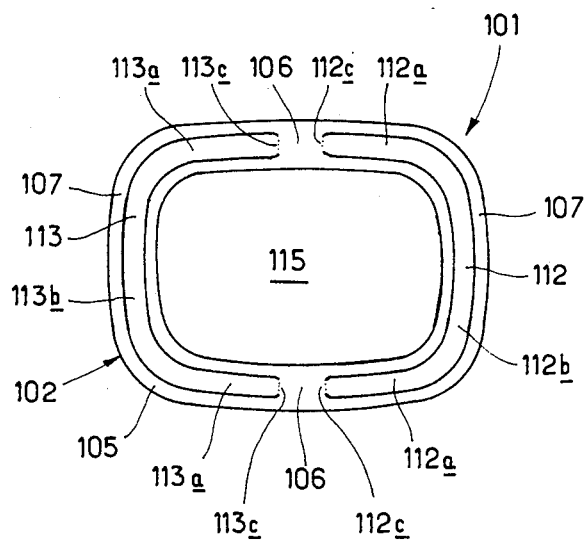
FIG. 6 shows a second mode of embodiment of an applicator-device according to the present invention, the said applicator-device being represented in the rest position, being put on its face having the absorbent pad.
Figure 7:
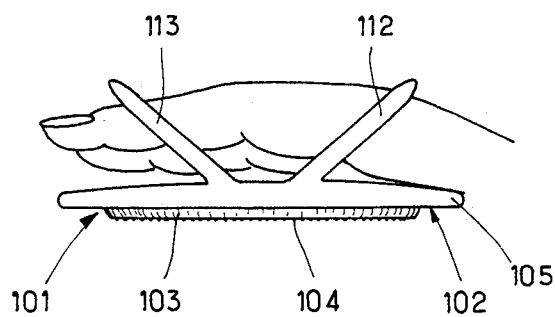
FIG. 7 represents a side view of the applicator-device of FIG. 6, in the position it occupies for the massage.

In FIGS. 6 and 7, there has been represented another mode of embodiment of the applicator device according to the invention. This applicator device 101 comprises on the one hand, a rectangular pad 103 similar to the pad 3 of the first mode of embodiment and on the other hand, an applicator 102 constituted by a rectangular pad with rounded corners which has an overall surface exceeding that of the pad 103 and which can be made of a material identical with that of the applicator 2.

The said pad 103 is fixed, for instance by bonding, at its face opposite to its very absorbent face 104, to the central zone 115 of the applicator 102 which thus constitutes a protection as regards cold for the palm of the user's hand at the time of application.

The zone of the remaining edge 105 which has the shape of a flat frame carries, on the opposite side to the pad 103, two U-shaped handles 112, 113 disposed symmetrically in relation to the transverse axis of the applicator 102. Each handle 112, 113 is fixed in the manner of an articulated film type hinge in the median region of the longitudinal sides 106 of the said applicator 102 at the end edges, 112c, 113c of its sides 112a, 113a, the edges 112c, 113c being disposed substantially parallel to the transverse axis of symmetry of the applicator 102. Thus, the arms 112a, 113a of the handles 112, 113 respectively are located in each other's extension, the webs 112b, 113b being disposed respectively opposite each other.

When the user wishes to effect a massage by means of the device in accordance with the first mode of embodiment described above, he inserts a pad 3 into the applicator 2, the flap 15 of the latter being open as represented in FIG. 2. He thens inserts a pad 3 by presenting it in the manner represented in FIG. 2 until the peripheral frame 3a of the said pad comes to be positioned on the edge of the said applicator 2. Subsequently, he turns down the flap 15, places one hand over the said flap 15 and he comes to fix the two flexible tabs 12 and 13 to each other ensuring their fixing with the required grip by the cooperation of the "hook", 14a and "velours" 14b parts on the palm of the hand.

By turning his hand round, the user presents the super absorbent face 4 of the pad 3, which can receive a dose of the composition delivered in the liquid state by the pressurised container 17, placed in the position represented in FIG. 5, because the output jet is liquid. By depression of the movable portion 21 which constitutes a push button of the dispensing head 19, in the direction of the arrow F, (FIG. 5) the liquid dose ejected (M) rapidly impregnates the whole surface 4 of the pad 3. The liquefied gas constituted by the mixture of the halogenated aliphatic hydrocarbons is ejected from the pressurised container 17 at a temperature of the order of −42° C. The face 4 having been impregnated, the user applies the device 1 to the skin, the liquefied gas retained by the superabsorbent face 4 then evaporating quite slowly above this face, producing a cold effect for approximately one minute.

As for the silicone and the volatile solvents which contain the active substance (or substances), they allow a liquid film to be deposited on the skin, which film will disappear when the skin will have regained its normal temperature.

The user thus recovers a hydrated skin, stimulated and soft after a prolonged contact with the cold, since the hydrating agent was capable of penetrating into the skin.

When the user wishes to effect a massage by means of the device in accordance with the second mode of embodiment described above, he slides one hand along the direction of the longitudinal axis of the applicator 102, between the plate carrying the absorbent pad 103 and the handles 112 and 113; the latter are raised to occupy the position represented in FIG. 7. By turning his hand round, the user presents the superabsorbent face of the pad 103 and he can then proceed as indicated above.

If reference is now made to FIG. 8, it will be seen that 201 designates an applicator device as a whole in accordance with a third mode of embodiment of the invention.

This device 201 comprises an applicator 202 which contains an elongate, slightly curved handle 224 which is extended in a sole 225 whose flat external surface 226 is capable of receiving a pad 203 of an absorbent material such as cellulose wadding, the said pad 203 being detachably fixed to the said surface 226, for instance by a fixing system of the "velcro" type or of a self adhesive type. This makes it possible to change the pad 203 after use.

The composition which is intended to be applied on the pad 203 is contained in a pressurised container 217 which has been represented in the position of use in FIG. 8.

This container 217 comprises a body 218 having a lateral wall comprising a cylindrical zone 227 wherewith it is joined to the flat bottom 228 of the said container 217 and a frustoconical upper zone 229, on the upper end edge whereof, there is fixed a valve carrier cup by means of a crimped rim 230. In the central zone of the valve carrier cup, there is disposed a valve provided with an emergent outlet tube 231. If the tube 231 is depressed, one causes the content of the container 217 to be exposed to the free air which content is projected from the latter in the form of a liquid jet to impregnate the pad 203 as will be described below.

The container 217 is inserted axially with its lower cylindrical portion 232 of a base 233 which comprises an extension 234 serving as support for the applicator 202 in its position of rest. For this purpose, the top 235 of the said extension 234 has a wall zone complementary to that of the applicator 202 laid down flat, its surface 226 being disposed horizontally and turned towards the said extension 234, in other words, a wall zone comprising a slightly convex region 236 corresponding to the handle 224 and a flat region corresponding to the said surface 226.

The extension 234 of the base 233 also has a reserve supply function for a plurality of pads 203. For this purpose, it comprises a parallelepiped cut out 238 issuing in one of its lateral walls which, in the example shown, allows three rows of three pads 203 to be inserted with a view to their storage.

The portion of the container 217 emerging from the base 233 receives a cap 239 constituted by two coaxial cylindrical skirts,—that is to say, an internal skirt 240 and an external skirt 241—longer than the preceding one—, joined to a flat annular top 242. The internal skirt 240 comprises at its free end an external annular groove 243 wherewith the cap 239 comes to be fastened on the crimped rim 230. As for the external skirt 241, in the fixed position of the cap 239, it comes to rest on an annular set back 244 cut in the cylindrical wall surrounding the recess 232 near its upper free edge.

On the outlet tube 231, a cup 245 comes to rest which has the function of a component controlling the actuation of the outlet valve of the pressurised container 217, the applicator device 201 serving for its part, as a push button, as will be described below.

The cup 245 comprises a slightly concave plate 246 whose concavity is turned towards the outside in the fitted position of the said cup 245, the latter comprising, starting from its convex wall on the one hand, a cylindrical skirt 250 disposed near the periphery of the latter and capable of sliding in the space delimited by the skirt 240 of the cap 239, being guided along the said skirt 240 and, on the other hand, a central extension 247 traversed by an axial duct 248 delimited by a cylindrical wall comprising, substantially at mid height, an annular shoulder 249 serving as stop for the free edge of the stem 231 when the cup 245 comes to surmount the said stem 231.

The composition contained in the pressurised container 217 can be identical with that described above.

When the user wishes to effect a massage by means of this device, he places the applicator 202 on the cup 245 as represented in FIG. 8 and he presses in the direction of the arrow f to open the valve of the pressurised container 217. The ejected liquid dose rapidly impregnates the whole pad 203, the liquefied gas constituted by the mixture of the halogenated aliphatic hydrocarbons is ejected from the pressurised container 217 at a temperature of the order of −42° C.

The user then applies the said pad 203 to the skin, the liquefied gas then evaporating quite slowly above this surface, producing a cold effect for approximately one minute, the active substance being deposited on the skin and penetrating into it after the volatile non-cryogenic substance has evaporated.

If reference is now made to FIG. 9, it will be seen that a unit in accordance with a fourth mode of embodiment of the invention has been designated by 301 whose elements which are identical to those of the third mode of embodiment have been marked on this figure by reference numerals increased by 100. Here, there will only be described the differences between these two modes of embodiment:

The setback 344 cut in the wall delimiting the recess 332 serves as support for a detachable cap 350 represented by dot dashes in FIG. 9 and whose skirt 351 comprises, along its free edge, an external bead 352 intended to be received by catch engagement in a peripheral annular groove 353 cut out above the set back 344.

In this mode of embodiment, the cup 245 of the first mode of embodiment is eliminated, the duct 348 being directly cut in the sole 325, perpendicular to the plane of the wall 326, the shoulder 349 for the bearing contact of the free edge of the stem 331, being parallel to the said wall 326. It will also be observed in FIG. 9 that the duct 348 opens out in the wall 326 via a flared zone.

The functioning of this device 301 is identical with that of the device 201, save that for impregnating the pad 303, the applicator 302 is presented as shown in FIG. 9. This impregnation is effected via the rear face of the pad 303. Thus the risks of fouling of the cup 245 are avoided, which fouling deposits would be redeposited on the face of the pad 303 in contact with the cutaneous covering.

In FIGS. 10 and 11, a device 401 has been represented in accordance with a fifth mode of embodiment, the elements being identically re-encountered in this mode of embodiment and the preceding one, bearing reference numerals increased by 100.

The applicator 402 is distinguished from the applicator 302 in that the sole 425 is made of two parts, that is to say, a top 457 and an opening 454 having the shape of cup without bottom, at the upper edge whereof, there is joined the handle 424 which is situated substantially in the upper plane of the said opening 454, curving slightly at its free end in the opposite direction to the latter. Moreover, the handle 424 comprises, in its zone of transition with the opening 454, an aperture 455 passing through it, with an axis substantially perpendicular to the median line of the said handle 424.

On the opposite side to the said aperture 455, the opening 454 is joined by means of a hinge 456 to a substantially flat circular shaped top 457 carrying in the region diametrically opposed to the hinge 456, a hook 458 intended to penetrate into the aperture 455 when the said top 457 is turned down and to come to secure the top 457 on the opening 454.

Moreover, the duct 448 is extended by a tube 448a on the side turned towards the inside of the opening 454; the latter carries on the same side, radial fins 459 regularly distributed at the periphery of the tube 448 and being joined to the latter as well as to the top 457. Furthermore, the surface envelope of the free edges of the fins 459 has the shape of a hemisphere.

In use, a pad 403 comes to be disposed in the opening 454, as shown in FIG. 10, the said pad 403 being retained by the internal edge of the said opening 454. Subsequently, the top 457 is folded down as indicated by the arrow F in FIG. 10: the fins 459 ensure the shaping of the pad 403 which then constitutes a spherical segment projecting from the opening 454 being substantially in the continuation of the external surface of the latter.

The impregnation of the pad is then effected as indicated with reference to FIG. 9.

FIG. 12 represents a sixth mode of embodiment of the unit in accordance with the invention according to which substantially the same sole (525) is re-encountered as the sole 425 of the preceding mode of embodiment, save that for the catch engagement of the top 557 and of the opening 554, this latter comprises a cut out 560 intended to receive a stud 561 of the said top 557.

The originality of this mode of embodiment lies in that the top 557 is extended on the opposite side to the fins 559 by a hollow kneed element 562, joined at one substantially frustoconical portion 563 at one end to the external edge of the said top 557, and forming at the other end a cylindrical portion 564 coming to surmount the pressurised container 517. The region 565 of the portion 563 being, in this position, above the stem 531 of the valve of the pressurised container 517, constitutes the equivalent of a push button actuating the ejection of a dose of the treatment composition (arrow F in FIG. 12). In the assembled position of the applicator device 501, the cylindrical portion 564 comes, in effect, to surmount the upper portion of the pressurised container 517, the tube 548a being extended in the kneed element 562 by a tube 548b bent at right angles, whose end on the opposite side to the tube 548a constitutes the duct 548, with the shoulder 549 which cooperates with the free edge of the stem 531.

The pressurised container 517 is inserted with its base into a bucket shaped receptacle 566 which is partly fitted in the part 564 when the applicator device 501 is in position ready for use so as to allow the said part 564 to slide when the push button 565 is manipulated.

The advantage of this mode of embodiment is to allow direct application of the cryogenic treatment composition on the cutaneous covering, the face in particular. Moreover, the applicator device 501 is rechargeable, by replacing the aerosol container 517 when the latter is empty.

In all the modes of embodiment which have just been described, it may been imagined that the aerosol container only contains liquefied refrigerant gas and that absorbent pads are used which are impregnated by an active substance coming from a separate container (for instance, a container fitted with a dispensing pump) or which have already been pre-impregnated by the said active substance.

It shall be duly understood that the modes of embodiment described above are in no way restrictive and may give rise to any desirable modifications without thereby departing from the scope of the invention; thus it is in particular that in the case of the first mode of embodiment described above, the flap 15 could be independent of the frame 5; or could, moreover, have catch engagement means complementary to the means carried by the said frame 5; or that the handles 112, 113 of the base 102 in accordance with the second mode of embodiment could be fixed to the frame 105 by bonding into the said frame 105.

I claim:

1. A method of applying at least one active substance to the cutaneous covering to produce a cryogenic treatment effect, said method comprising storing at least one liquefied refrigerant gas in a pressurised container, impregnating an absorbent element by releasing a jet of liquid refrigerant from said container, said absorbent element also being impregnated with the said at least one active substance, subsequently applying said impregnated absorbent element to the cutaneous covering to be treated, and allowing said at least one refrigerant gas to evaporate slowly to produce the desired cryogenic effect and to leave a film of the said at least one active subtance on said cutaneous covering.

2. A method according to claim 1, wherein both said at least one liquefied refrigerant gas and said at least one active substance are stored in said pressurised container for simultaneous release to impregnate said absorbent element.

3. A method according to claim 1, wherein said at least one active substance and said at least one liquefied refrigerant gas are stored separately and that they are transferred successively to the absorbent element.

4. A method according to claim 1, wherein at least one volatile non-cryogenic substance, capable of solubilising the at least one active substance, is stored with the said at least one liquefied refrigerant gas, the said liquefied refrigerant gas forming a long lasting phase for the resultant composition ejected from the pressurised container, the said volatile non-cryogenic substance or substances evaporating when the cutaneous covering regains its normal ambient temperature.

5. A method according to claim 4, wherein the at least one non-cryogenic substance comprises 3 to 35% by weight of the contents of the pressurised container in relation to the weight of the liquefied refrigerant gas.

6. A method according to claim 5, wherein the said at least one non-cryogenic substance comprises 10 to 30% by weight of the liquefied refrigerant gas in the container.

7. A method according to claim 1, wherein the liquefied refrigerant gas are chosen from the halogenated aliphatic hydrocarbons.

8. A method according to claim 4, wherein the volatile non-cryogenic substance comprises a volatile silicone derivative.

9. A method according to claim 1, wherein the said at least one active substance is a skin care substance taken from the group formed by the hydrating, regenerative, anti-wrinkle, anti-acne, anti-cellulitic, hyperaemic and firming agents.

10. A method according to claim 1, wherein the at least one active substance is present in the form of a solution chosen from the group of aqueous or hydroalcoholic solutions.

11. A method according to claim 1, wherein the at least one active substance is in frozen form at the time of use.

* * * * *